United States Patent [19]

Morelle et al.

[11] 4,112,085
[45] Sep. 5, 1978

[54] METALLIC COMPOSITIONS

[76] Inventors: Jean V. Morelle; Eliane M. T. Lauzanne-Morelle, both of 170 Avenue Parmentier, 75010 Paris, France

[21] Appl. No.: 855,050

[22] Filed: Nov. 25, 1977

Related U.S. Application Data

[62] Division of Ser. No. 621,954, Oct. 14, 1975.

[30] Foreign Application Priority Data

Oct. 28, 1974 [FR] France .................. 74 35929

[51] Int. Cl.² .................. A61K 31/555; A61K 31/28; A61K 31/16
[52] U.S. Cl. .................. 424/245; 424/287; 424/289; 424/294; 424/295; 424/318; 424/319; 424/320; 424/324
[58] Field of Search .............. 424/245, 287, 289, 294, 424/295, 318, 319, 320, 324

[56] References Cited

U.S. PATENT DOCUMENTS 3,950,529   4/1976   Fischer et al. .................. 424/319

Primary Examiner—Sam Rosen
Attorney, Agent, or Firm—Eyre, Mann, Lucas & Just

[57] ABSTRACT

The invention relates to new compositions of the formula:

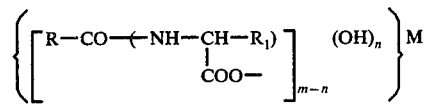

wherein:
R—CO is the acyl moiety of a straight fatty acid RCOOH comprising from 6 to 20 carbon atoms.

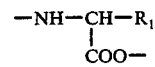

represents either the skeleton of the amino acid

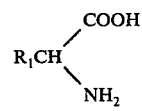

in which $R_1$ is conventionally used to allow the generic designation of any of the naturally occurring α amino acids obtained by degradation of the various proteins, or the ensemble of skeletons of all the α aminoacids obtained by complete hydrolysis of the natural proteins, said compositions containing the alpha aminoacids in proportions similar to that ones existing in the proteins treated.
M is a metal selected from within: magnesium, calcium iron, cobalt, manganese, copper, zinc, molybdenum and aluminum.
$m$ is the valency of the selected M.
$n$ is an integer inferior to $m$.
Some detailed examples of compositions are given.

2 Claims, No Drawings

METALLIC COMPOSITIONS

This is a division of application Ser. No. 621,954, filed Oct. 14, 1975.

This invention relates to new metallic compositions of matter presenting specially an interest in the field of treatment of men, animals and plants.

It is well-known that discrete amounts of metals can be met in all living organisms (human beings, animals, plants) and that they constitute, in all the cases, indispensable elements. The metals are generally encountered under the form of protidic complexes (metalloproteins), glucido protidic or lipido protidic complexes.

These metallic structures play a specific role which varies with the nature of the metal and with the structures of the complexing molecule itself; their action occurs in the field of biocatalysis or in the metabolic exchanges which allow the survival or the growing of the organs or of the organisms.

The major problem lies in the appropriate selection of the complexing structures which must be of such a nature as to allow an acceptable assimilation or absorption by the organ or the organism.

It is well-known that lipoaminoacids and lipopolyaminoacids can easily go through the tissues and cellular membranes due to their specific lipo protidic structures fully compatible with those tissues; although water-insoluble, these lipoaminoacids and lipopolyaminoacids are nevertheless entitled of a certain ionisation capacity which comes from the carboxylic group in alpha position of the amino group; similarly the water insoluble salts of the lipoaminoacids present the same characteristics while bringing together the selected metal.

Accordingly this invention provides the new composition of matter of the formula:

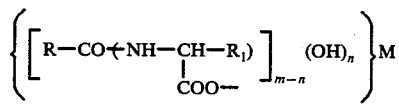

wherein:

R-CO is the acyl moiety of a straight fatty acid RCOOH comprising from 6 to 20 carbon atoms.

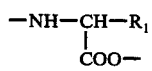

represents either the skeleton of the amino acid

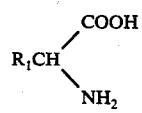

in which $R_1$ is conventionally used to allow the generic designation of any of the naturally occurring α amino acids obtained by degradation of the various proteins, or the ensemble of skeletons of all the α aminoacids obtained by complete hydrolysis of the natural proteins, said compositions containing the alpha aminoacids in proportions similar to that ones existing in the proteins treated.

M is a metal selected from within: magnesium, calcium, iron, cobalt, manganese, copper, zinc, molybdenum and aluminium.

$m$ is the valency of the selected M $n$ is an integer inferior to $m$.

The metals retained hereinabove have been specially selected for they are normal constituents of human, animal or vegetable tissues and not toxic to these tissues. Molybdenum and zinc are to be used only in preparations for the treatment of plants whereas all the others are suitable for compositions for the treatment of human and animal tissues.

This invention provides for instance compositions to be used in human and animal therapies for the correction of deficiencies in some of the metals above indicated (preferred forms of administration are creams, ointments and gelatin capsules for instance) and compositions to be used in the treatment of plants which could be presented under the form of aqueous emulsions.

Some examples of formulations are given below:

| I.- Creams for Topical Use (proportions in weights) | | |
|---|---|---|
| A/ | Magnesium palmitoyl collagenate | 5 |
| | Polyethylene cetylic alcohol | 5 |
| | Glycerine | 5 |
| | Stearine | 7 |
| | Isopropylpalmitate | 10 |
| | Conservative agent | q.s. |
| | water q.s. | 100 |
| B/ | Magnesium caprylylglycinate | 5 |
| | Polyethylene cetylic alcohol | 5 |
| | Glycerine | 5 |
| | Stearine | 7 |
| | Isopropylpalmitate | 10 |
| | Conservative agent | q.s. |
| | Water q.s. | 100 |
| C/ | Calcium palmitoyl collagenate | 5 |
| | Polyethylene cetylic alcohol | 5 |
| | Glycerine | 5 |
| | Stearine | 7 |
| | Isopropylpalmitate | 10 |
| | Conservative agent | q.s. |
| | Water q.s. | 100 |
| II.- Preparations for Oral Administration | | |
| A/ | Iron palmitoyl collagenate | 0.250 g |
| | Lactose | 0.050 g |
| | (for a gelatin capsule of 0.3 g) | |
| B/ | Manganese palmitoylglycinate | 0.250 g |
| | Lactose | 0.050 g |
| | (for a gelatin capsule of 0.3 g) | |
| C/ | Cobalt palmitoyl methionate | 0.250 g |
| | Lactose | 0.050 g |
| | (for a gelatin capsule of 0.3 g) | |
| III.- For Use in Agriculture (Proportions in weights) | | |
| | Copper caprylyl methionate | 5 |
| | Polyoxyethylene cetylic alcohol | 10 |
| | Water q.s. | 100 |

These metallic complexes may be prepared either by double decomposition between their soluble salts (alkaline metal salts) and the appropriate metallic soluble salt or by neutralization of the free carboxy group by a base or a metal hydrate. This well-known reactions need no specific description and lead to water insoluble substances which, after precipitation, filtration, washing and drying, give products, the specifications of which are reported in following tables where the compounds are classified by the selected metals.

A-ALUMINIUM SALTS

No 1-Caprylylglycinate

[CH$_3$—(CH$_2$)$_6$—CO—NH—CH$_2$—COO]$_2$ AlOH Molecular weight : 444

No 2-Caprylylcollagenate

[CH$_3$—(CH$_2$)$_6$—CO—(NH—CHR$_1$)]Al (OH)$_2$ M.W. : 307
                                    |
                                    COO—

-continued wherein —(NH—CHR₁) represents conventionally the
        |
       COO— skeletons of the ensemble of the aminoacids obtained
by the hydrolysis of collagene.

No 3-Caprylylcystinate

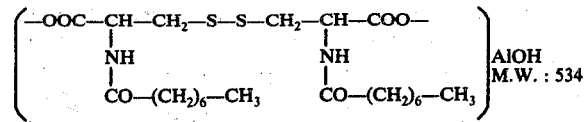 AlOH M.W.: 534

No 4-Caprylylmethionate

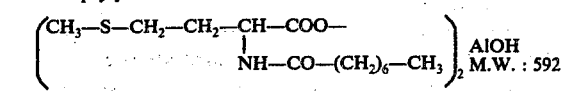 AlOH M.W.: 592

No 5-Palmitoylmethionate

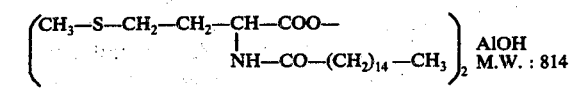 AlOH M.W.: 814

| Ref. No. | % of Metal A | B | M.P. | % of Nitrogen on the lipo aminoacid A | B | on the salt A | B | Aspect |
|---|---|---|---|---|---|---|---|---|
| 1 | 6.1 | 6.5 | 240° | 6.9 | 6.8 | 6.3 | 6.1 | white powder |
| 2 | 8.8 | 9.6 | +300° | 5.7 | 5.4 | 4.5 | 4.2 | " |
| 3 | 6.2 | 7.1 | +300° | 5.7 | 5.4 | 5.2 | 4.8 | " |
| 4 | 4.5 | 4.8 | 184° | 5.1 | 4.7 | 4.6 | 4.3 | " |
| 5 | 3.3 | 3.2 | 66° | 3.6 | 3.2 | 3.4 | 3.1 | " |

A = Theoritical percentage
B = Found percentage
M.P. = melting point in Celsius degrees

B-CALCIUM SALTS

No 6-Caprylylglycinate
  $(CH_3-(CH_2)_6-CO-NH-CH_2-COO)_2$ Ca M.W.: 442

No 7-Dipalmitoylhydroxyprolinate

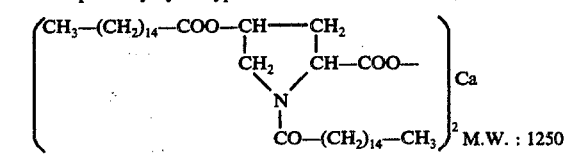 M.W.: 1250

No 8-Palmitoylcollagenic

 Ca M.W.: 758 please refer to compound number 2 for the
understanding of —(NH—CHR₁)
              |
             COO—

No 9-Palmitoylcaseinic
  [CH₃—(CH₂)₁₄—CO—(NH—CHR₁)]₂ Ca M.W.: 816
                    |
                   COO— definition of —(NH—CHR₁) comparable to compound 8
            |
           COO—
except that collagene is replaced by caseine No 10-Caprylcollagenate
  [CH₃—(CH₂)₆—CO—(NH—CHR₁)]₂ Ca M.W.: 532
                  |
                 COO—
Same definition as in compound 8.

No 11-Caprylylcystinate

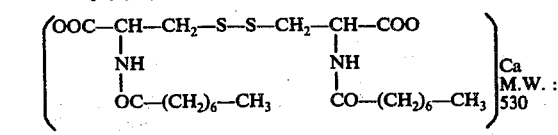 Ca M.W.: 530

No 12-Lauroylcollagenate
  [CH₃—(CH₂)₆—CO—(NH—CHR₁)]₂ Ca M.W.: 644
                  |
                 COO— same definition as in compound 8.

| Ref. No. | % of Metal A | B | M.P. | % of Nitrogen on the lipo aminoacid A | B | on the salt A | B | Aspect |
|---|---|---|---|---|---|---|---|---|
| No 6 | 9.1 | 8.4 | 250° | 6.9 | 6.8 | 6.3 | 5.9 | white powder |
| No 7 | 3.2 | 3.6 | 155° | 2.3 | 2.1 | 2.2 | 2.1 | " |
| No 8 | 5.3 | 4.9 | 170° | 3.9 | 3.6 | 3.7 | 3.5 | " |
| No 9 | 4.9 | 3.8 | 145° | 3.6 | 3.1 | 3.4 | 2.9 | " |
| No 10 | 7.5 | 6.8 | 172° | 5.7 | 5.4 | 5.2 | 4.9 | " |
| No 11 | 7.5 | 8.4 | +250° | 5.7 | 5.4 | 5.2 | 4.7 | " |
| No 12 | 6.2 | 5.4 | 105° | 4.6 | 4.3 | 4.3 | 4.1 | " |

A = Theoritical percentage
B = Found percentage
M.P. = melting point in Celsius degrees

C-COBALT SALTS

No 13-Palmitoylcollagenate
  [CH₃—(CH₂)₁₄—CO—(NH—CHR₁)]₂ Co M.W.: 777
                    |
                   COO—
same definition as in example 2

No 14-Palmitoylmethionate

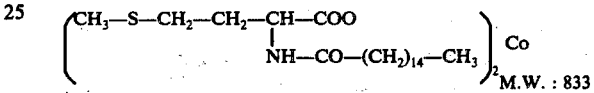 Co M.W.: 833

No 15-Caprylylcystinate

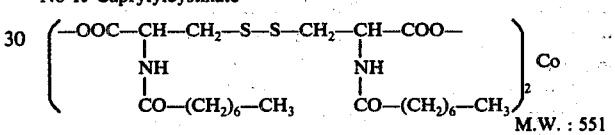 Co M.W.: 551

No 16-Undecylenoylglycinate
  (CH₂=CH—(CH₂)₈—CO—NH—CH₂—COO)₂ Co M.W.: 539

No 17-Lauroylglycinate
  (CH₃—(CH₂)₆—CO—NH—CH₂—COO)₂ Co M.W.: 571

| Ref. No. | % of Metal A | B | M.P. | % of Nitrogen on the lipo aminoacid A | B | on the salt A | B | Aspect |
|---|---|---|---|---|---|---|---|---|
| No 13 | 7.6 | 8.2 | 105° | 3.9 | 3.6 | 3.6 | 3.2 | violet pink powder |
| No 14 | 7.1 | 7.8 | 123° | 3.6 | 3.2 | 3.3 | 3.1 | " |
| No 15 | 10.7 | 11.5 | 240° | 5.7 | 5.2 | 5.1 | 4.9 | " |
| No 16 | 10.9 | 9.2 | 168° | 5.8 | 5.4 | 5.2 | 4.7 | " |
| No 17 | 10.3 | 9.3 | 145° | 5.4 | 4.8 | 4.4 | 4.1 | " |

A = Theoritical percentage
B = Found percentage
M.P. = melting point in Celsius degrees

D-COPPER SALTS

No 18-Caprylylglycinate
  (CH₃—(CH₂)₆—CO—NH—CH₂—COO)₂ Cu M.W.: 463

No 19-Caprylylmethionate

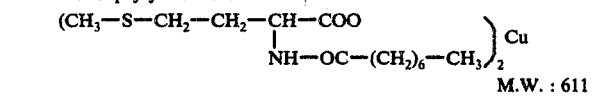 Cu M.W.: 611

No 20-Palmitoylcollagenate
  [CH₃—(CH₂)₁₄—CO—(NH—CHR₁)]₂ Cu M.W.: 781
                    |
                   COO—
please refer to compound number 2 for the
understanding of —(NH—CHR₁)
              |
             COO—

No 21-Palmitoylkeratinic
  [CH₃—(CH₂)₁₄—CO—(NH—CHR₁)]₂ Cu M.W.: 821
                    |
                   COO—

-continued

Definition comparable to compound 20
except that collagene is replaced by keratine No 22-Caprylcollagenate $$[CH_3-(CH_2)_6-CO-(NH-\underset{\underset{COO-}{|}}{CHR_1})]_2 Cu \quad M.W.: 555$$

Same definition as in example 20

No 23-Lauroylcollagenate $$[CH_3-(CH_2)_{10}-(NH-\underset{\underset{COO-}{|}}{CHR_1})]_2 Cu \quad M.W.: 669$$

Same definition as in example 20

No 24-Oleyl collagenate of copper $$[CH_3-(CH_2)_7-CH=CH-(CH_2)_7-CO-(NH-\underset{\underset{COO-}{|}}{CHR_1})]_2 Cu$$

Same definition as in example 20 M.W.: 829

| Ref. No. | % of Metal A | B | M.P. | % of Nitrogen on the lipo aminoacid A | B | on the salt A | B | Aspect |
|---|---|---|---|---|---|---|---|---|
| No 18 | 13.5 | 11.8 | 170° | 6.9 | 6.7 | 6 | 5.7 | green powder |
| No 19 | 10.3 | 9.7 | 180° | 5.1 | 4.7 | 4.6 | 4.3 | " |
| No 20 | 8.1 | 7.3 | 85° | 3.7 | 3.5 | 3.6 | 3.2 | " |
| No 21 | 7.7 | 6.9 | 80° | 3.7 | 3.4 | 3.4 | 3.1 | " |
| No 22 | 11.4 | 9.8 | 145° | 5.7 | 5.4 | 5.0 | 4.7 | green powder |
| No 23 | 9.5 | 8.6 | 90° | 4.6 | 4.3 | 4.2 | 3.8 | " |
| No 24 | 7.6 | 6.9 | 55° | 8.1 | 7.4 | 3.1 | 2.8 | " |

A = Theoritical percentage
B = Found percentage
M.P. = melting point in Celsius degrees

E-IRON SALTS

No 25-Palmitoylcollagenate $$[CH_3-(CH_2)_{14}-CO-(NH-\underset{\underset{COO-}{|}}{CHR_1})]_2 Fe \quad M.W.: 774$$

please refer to compound number 2 for the understanding of $-(NH-\underset{\underset{COO-}{|}}{CHR_1})$ No 26-Caprylylcollagenate $$[CH_3-(CH_2)_6-CO-(NH-\underset{\underset{COO-}{|}}{CHR_1})]_2 Fe \quad M.W.: 550$$

same definition as in example 25

F-ZINC SALTS

No 27-Caprylylglycinate $$[CH_3-(CH_2)_6-CO-(NH-\underset{\underset{COO-}{|}}{CHR_1})]_2 Zn \quad M.W.: 465$$

please refer to compound 2 for the understanding of $-(NH-\underset{\underset{COO-}{|}}{CHR_1})$

G-MANGANESE SALTS

No 28-Palmitoylcollagenate $$[CH_3-(CH_2)_{14}-CO-(NH-\underset{\underset{COO-}{|}}{CHR_1})]_2 Mn \quad M.W.: 773$$

please refer to compound 2 for the understanding of $-(NH-\underset{\underset{COO-}{|}}{CHR_1})$ No 29-Caprylylglycinate $$[CH_3-(CH_2)_6-CO-(NH-\underset{\underset{COO-}{|}}{CHR_1})]_2 Mn \quad M.W.: 455$$

Same definition as in example 28

| Ref. No. | % of Metal A | B | M.P. | % of Nitrogen on the lipo aminoacid A | B | on the salt A | B | Aspect |
|---|---|---|---|---|---|---|---|---|
| No 25 | 7.23 | 6.46 | 90° | 3.9 | 3.6 | 3.6 | 3.2 | red ochre powder |
| No 26 | 10.1 | 9.2 | 130° | 5.7 | 5.4 | 5.1 | 4.6 | " |
| No 27 | 13.9 | 12.8 | 200° | 7.0 | 6.2 | 6.0 | 5.1 | white powder |
| No 28 | 7.1 | 6.7 | 97° | 3.9 | 3.6 | 3.6 | 3.2 | beige powder |
| No 29 | 12 | 13.2 | 199° | 6.9 | 6.8 | 6.1 | 5.8 | " |

A = Theoritical percentage
B = Found percentage
M.P. = melting point in Celsius degrees

H-MAGNESIUM SALTS

No 30-Palmitoylcollagenate $$[CH_3-(CH_2)_{14}-CO-(NH-\underset{\underset{COO-}{|}}{CHR_1})]_2 Mg \quad M.W.: 742$$

please refer to compound number 2 for the understanding of $-(NH-\underset{\underset{COO-}{|}}{CHR_1})$ No 31-Caprylylcollagenate $$CH_3-(CH_2)_6-CO-(NH-\underset{\underset{COO-}{|}}{CHR_1})]_2 Mg \quad M.W.: 518$$

same definition as in example 30

No 32-Palmitoylmethionate

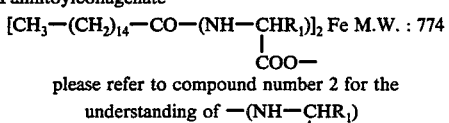

No 33-Caprylylmethionate

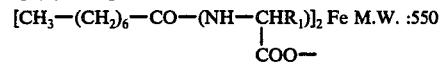

No 34-Caprylylglycinate
$(CH_3-(CH_2)_6-CO-NH-CH_2-COO)_2 Mg \quad M.W.: 424$

No 35-Lauroylaspartate

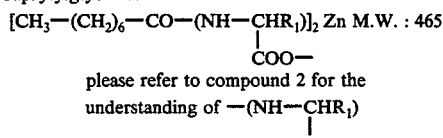

No 36-Caproylglycinate
$(CH_3-(CH_2)_4-CO-NH-CH_2-COO)_2 Mg \quad M.W.: 368$

| Ref. No. | % of Metal A | B | M.P. | % of Nitrogen on the lipo aminoacid A | B | on the salt A | B | Aspect |
|---|---|---|---|---|---|---|---|---|
| No 30 | 3.2 | 2.6 | 99° | 3.9 | 3.6 | 3.8 | 3.4 | White powder |
| No 31 | 4.6 | 4.2 | 185° | 5.7 | 5.4 | 5.4 | 4.8 | " |
| No 32 | 3.0 | 2.7 | 157° | 3.6 | 3.3 | 3.5 | 3.2 | " |
| No 33 | 4.2 | 3.8 | 200° | 5.1 | 4.7 | 4.9 | 4.7 | " |
| No 34 | 5.6 | 5.2 | 185° | 6.9 | 6.8 | 6.6 | 6.2 | " |
| No 35 | 7.1 | 7.8 | >200° | 4.4 | 4.1 | 4.1 | 3.8 | " |
| No 36 | 6.5 | 5.9 | >200° | 8.1 | 7.4 | 7.6 | 7.1 | " |

A = Theoritical percentage
B = Found percentage
M.P. = melting point in Celsius degrees The compositions according to this invention may be used, for instance:

for those containing calcium salts, for the treatment of affections in relationship with the teeth and the bones;

for those containing aluminium salts in hygienic preparations acting against the sudation;

for those containing cobalt salts, as hemato poietic factors;

for those containing manganese and magnesium salts, as growing factors more particularly for cattle;

for those containing copper salts, as biosynthetic (synthesis of cuproproteins) and in the treatment of cryptogamic diseases.

We claim:

1. A composition of the formula

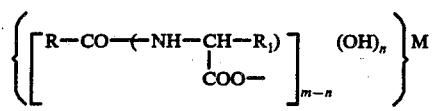

wherein:
(a) R-CO is the acyl moiety of a straight fatty acid RCOOH comprising from 6 to 20 carbon atoms;

represents the ensemble of skeletons of all the aminoacids obtained by complete hydrolysis of the natural proteins, said compositions containing the alpha aminoacids in proportions similar to those ones existing in the proteins treated;
(c) M is a metal selected from the group consisting of magnesium, calcium, iron, cobalt, manganese, copper, zinc, molybdenum and aluminium;
(d) $m$ is the valency of the selected M; and
(e) $n$ is an integer inferior to $m$.

2. A therapeutic composition for the treatment of deficiencies in metal in living organisms, said therapeutic composition comprising a carrier and an effective amount of the composition of claim 1.

* * * * *